United States Patent [19]

Williams

[11] Patent Number: 4,881,525
[45] Date of Patent: Nov. 21, 1989

[54] CERVICAL FUSION RETRACTOR
[76] Inventor: Richard C. Williams, 55 Highland Dr., San Luis Obispo, Calif. 93401
[21] Appl. No.: 242,634
[22] Filed: Sep. 9, 1988

Related U.S. Application Data
[63] Continuation-in-part of Ser. No. 50,150, May 14, 1987, abandoned.

[51] Int. Cl.⁴ ............................................... A61B 17/02
[52] U.S. Cl. ........................................ 128/20; 623/17
[58] Field of Search ................... 128/17, 18, 19, 20, 128/345, 3

[56] References Cited
U.S. PATENT DOCUMENTS
1,506,032  8/1924  Stevens ................................. 128/17
2,075,534  3/1937  McCormack ........................ 128/17
3,916,907  11/1975  Peterson .............................. 128/345

FOREIGN PATENT DOCUMENTS
1051455  2/1959  Fed. Rep. of Germany ........ 128/17
2080113  2/1982  United Kingdom .................. 128/20

Primary Examiner—Edward M. Coven
Assistant Examiner—Mark S. Graham
Attorney, Agent, or Firm—Grant L. Hubbard

[57] ABSTRACT

A tissue retractor for use in surgical procedures comprising a pair of elongate retractor mounting members pivotally connected at proximal ends to permit relative articulation and to clamp the mounting members at any selected angle relative to each other with retractor securing elements mounted on the respective retractor mounting members for movement reciprocally along the length of the retractor mounting members and positioning the retractor securing means at a selected point there upon is disclosed.

3 Claims, 3 Drawing Sheets

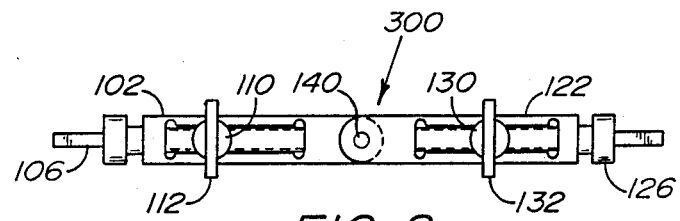
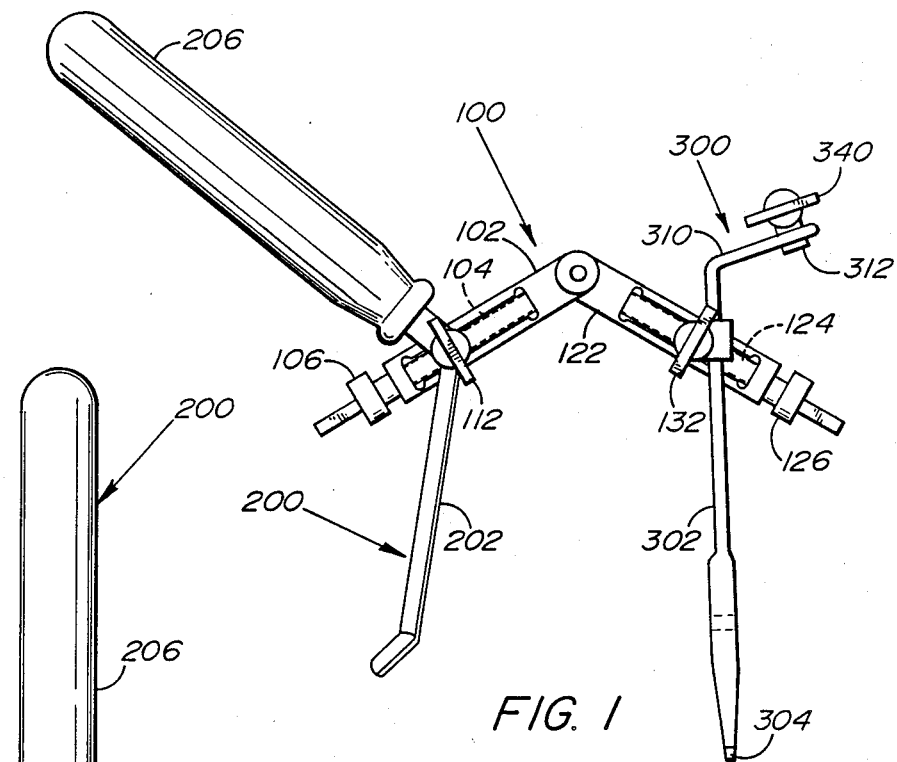
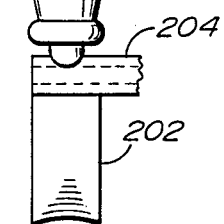
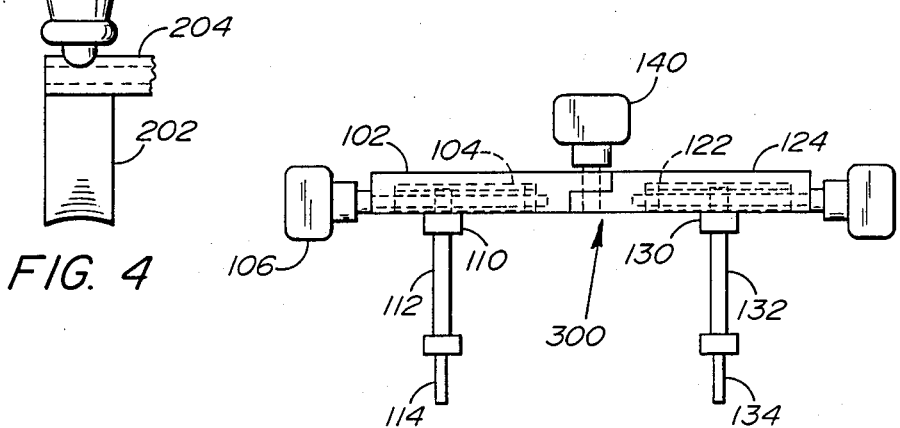

(54)

CERVICAL FUSION RETRACTOR

CROSS-REFERENCE TO COPENDING APPLICATION

This is a continuation-in-part of copending U.S. Patent Application Ser. No. 07/050,150, Filed May 14, 1987, now abandoned, to which priority is claimed.

FIELD OF THE INVENTION

This invention relates to surgical procedures generally and specifically to surgical equipment and, still more specifically, to retractor appliances fo surgery on the back and for cervical fusion surgery in particular.

BACKGROUND OF THE INVENTION

Anterior cervical fusion has been an accepted procedure for the treatment of cervical disk herniation as well as cervical spondylosis with associated cervical stenosis.

A microsurgical saw for carrying out this kind of procedure is described in U.S. Pat. appliction Ser. No. 026,038, filed Mar. 16, 1987 now U.S. Pat. No. 4,827,615.

The procedure with which this invention is described more fully hereinafter; briefly, however, the procedure is carried out, after preparation of a sterile field, by making a suitable incision, 3 to 4 cm, in the right anterior cervical area. The platysma muscle is identified and incised diagonally in the plane of its fibers and retracted laterally. The plane of dissection is then developed medial to the carotid sheath and lateral to the midline structures. Manual soft tissue retractors are placed superior to the longus colli musculature bilaterally. The bipolar cautery is then used to cauterize the venous plexus usually present at the margine of the longus colli muscle bilaterally. The longus colli muscle is elevated bilaterally and, according to the present invention, a self-retaining retractor as described hereinafter is hooked under the muscle bilaterally.

While there are many retractors available to the surgeon, none is entirely suitable for cervical fusion microsurgical procedures. It is a feature of this invention to provide a retractor, especially constructed and adapted to perform the muscular retraction operations involved in microsurgical anterior cervical fusion operations.

SUMMARY OF THE INVENTION

The present invention comprises a specialized retractor which can be dialed to the desired tension and the retractor blades articulated to achieve optimum exposure.

The invention comprises in one form, a complete assembly involving a pair of articulated supports for retracting hooks and/or retracting expansion forceps.

Another feature of the invention is to provide retracting expansion forceps suitable for use with the articulated mechanism of this invention or otherwise.

The present invention is a tissue retractor for use in surgical procedures comprising pair of elongate retractor mounting members each having a proximal and a distal end, means connecting the proximal ends of the respective retractor support members pivotally together to permit relative articulation between such members and to clamp such members at any selected angle relative to each other's retractor securing means and means mounting the retractor securing means on the respective retractor mounting members for movement reciprocally along the length of the retractor mounting members and positioning the retractor securing means at a selected point there upon.

In a more specific embodiment the invention comprises a tissue retractor for surgical use comprising first and second elongate mounting bars each having a proximal end and a distal end, pivot means mounting the proximal end of the mounting bars together for relative articulation retractor holders for mounting tissue retractors to the respective retractor mounting members, adjustable securing members mounting the retractor holders to the respective mounting members and for moving the securing members to selected positions along the length of mounting members and retractors secured to the retractor holders; the components of the retractor being so configured and constructed as to permit either of the retractors to be moved independently of the other along the length of the mounting members and for adjusting the angular relationship of the mounting members.

In one specific embodiment at least one tissue retractor comprises a pair of elongate retractor arms each having a proximal end and a distal end, pivot means securing adjacent sides of the retractor arms to each other between the ends of the retractor arms, means on the distal ends of the retractor arms for engaging and hooking the tissue of a patient, when the retractor is in use means connecting the proximal ends of the retractor arms together and for moving the proximal ends toward and away from each other, the retractor components being so constructed and configured that movement of the proximal end of the retractor arms together moves the distal ends thereof apart and movement of the proximal ends apart moves the distal ends together.

BRIEF DESCRIPTION OF THE DRAWINGS

FIG. 1 depicts an assembly drawing showing the articulated assembly of this invention having mounted thereupon the retracting hook and the retracting expansion forceps of this invention.

FIG. 2 is a side view of the articulated support mechanism of this invention.

FIG. 3 is a top view of the articulated support mechanism, using the view of FIG. 1 as a reference.

FIG. 4 is a face view of the retracting hook of this invention.

FIGS. 10 through 13 are provided to aid in the description and understanding of the procedure in which the present invention finds greatest advantage.

FIG. 12 depicts the final graft showing the two bone components tied together.

FIG. 13 depicts the placement of the graft in the bone incision, from the sagittal and AP views.

DESCRIPTION OF THE PREFERRED EMBODIMENT

Figure 5:
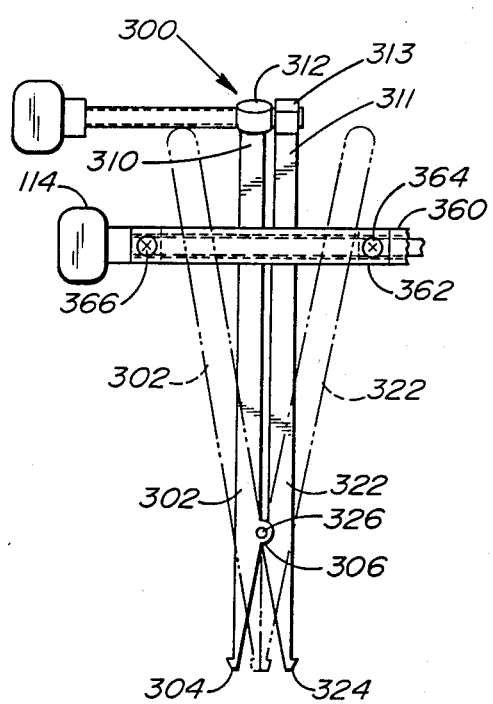
FIG. 5 is a front view of the retractor forceps of this invention showing the retractor structure in solid line with an alternative position in phantom line.
Figure 6:
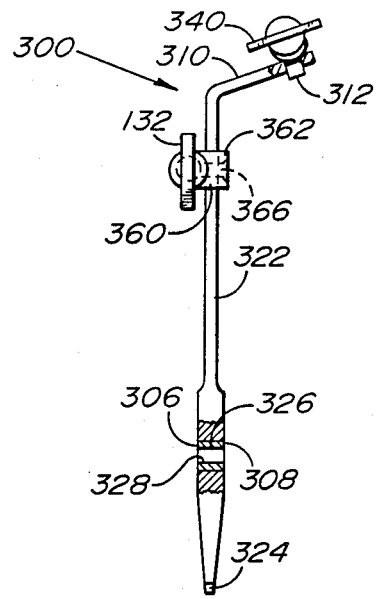
FIG. 6 is a side view of the retractor forceps of this invention in partial cutaway to show the hinging mechanism.
Figure 7:
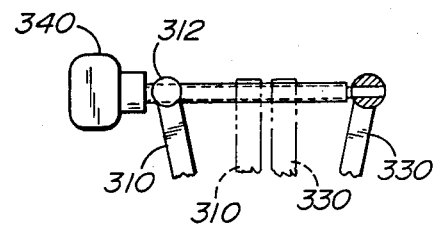
FIG. 7 is a view of the mechanism used to expand the forceps showing the forceps in partial view and partially cut away.

In making the following description, it will be understood that an exemplary and preferred embodiment is disclosed and described in detail, but that this embodiment is only exemplary and is not the only embodiment and is not limiting as to the scope of the invention.

Referring first to FIG. 1, the invention is an articulated adjustable retracting device 100. The device comprises a first mounting bar 102 having a slot 140 therein, in which a threaded bolt 106 is received and is held by a suitable keeper, lock nut or other device and which is provided with a handle on the distal end for turning the screw in the slot.

A retractor holder 110, a suitable bolt 112 with a handle 114 is provided for securing the retractors to the mounting bar.

A mirror image of the first retracting bar is shown as retracting bar 122 having a slot 124, threaded screw 126, retractor mount or carrier 130, and a screw 132 with a handle 134 for securing a retractor to the bar, as described previously. The proximal ends of the mounting bars 102 and 122 are pivotally mounted together by a screw 140 which allows the members or bars to articulate with respect to each other and to be clamped in any desired angular relationship with respect to each other. One angular relationship is shown in FIG. 1. FIGS. 2 and 3 show the angular relationship as linear, i.e. the axis of both of the bars are congruent.

Figure 9:
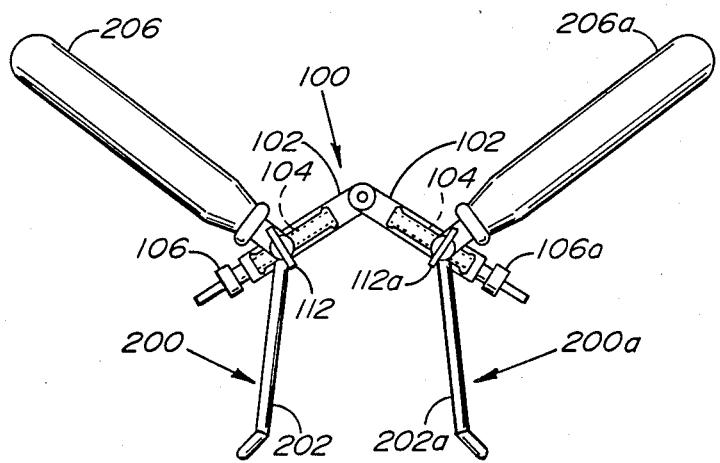
FIG. 9 is a side view of an alternative assembly of the invention in which a pair of muscle or tissue retractors are usd.
Figure 8:
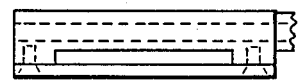
FIG. 8 is a top view of the mechanism for securing the expanding forceps of this invention to the articulated structure.

While any number of retractors may be utilized, one very convenient retractor is shown at 200 in FIGS. 1 and 4, and comprises a retractor blade 202 which is, in cross-section, a portion of a arc and is curved at the bottom to provide a hook for reaching under the muscles to be retracted. The blade 202 is connected to a pivot and lock sleeve 204 which is held in place, as shown in FIG. 1 by the bolt 112. Knots or knurled ends are provided to lock the retractor in the precise angular relationship desired. A handle 206 is provided on the other side of the sleeve to permit the surgeon to manipulate the blade to the desired location and then to lock it in place using the bolt 112 and the handle 114. FIG. 9 depicts one assembly in which two retractors of the type described are used. The retractor 200a a comprising retractor blade 202a connected to a pivot and lock sleeve 104 and bolt 112a and handle 114a is simply a mirror image of the retractor 200. The first and second retractors 200a and 200 are secured by the respective retractor mounting members to the respective retractor support members. These first and second retractors each comprise an elongate laterally arcuate blade having a convex surface. Longitudinally these retractors have a generally straight elongate main portion and an end portion curved relative to the main portion, and a handle, the handle being mounted to the blade. When used as a pair, as shown in FIG. 9, the curved end portions and the convex surfaces of the first and second retractors face relatively opposite to one another.

Another desired and most sophisticated retractor is shown as the assembly 300 in FIGS. 1, 5, 6, 7 and 8. This retractor comprises a pair of elongate retractor arms one of which is 302 provided at the distal end 304 with means for engaging or hooking the muscle to be retracted and comprising a hinge or pivot structure including two extended, apertured elements 306 and 308, best shown in the cut away view of FIG. 6 and in FIG. 5. The proximal end of the amr 310 is preferably bent to the side and a threaded nut 312 is secured to the proximal end 310 of the arm 302. The invention is operable with the bend to the left as viewed in FIG. 6, but is much easier handled with the bend to the right as shown in the drawing. An arm 322 is in large measure a mirror image of the amr 302, the arm 322 comprising a like distal end 324 for engaging the soft tissue or muscle to be spread apart, or the bone structure to be spread apart as may be desired, but the hinge mechanism being slightly different involving one apertured extension 326. The proximal end of arm 322, shown at 330 in bent in like manner as previously described and carries a threaded nut 313 there upon. A threaded bolt 340 with a handle on the end extends through and engages the threads of the two threaded nuts 312 and 313. By twisting the handle, the proximal end of the retractor arms may be spread apart of brought together. Spreading apart the proximal end of the arms 302 and 322 brings the distal ends close together and, as shown in FIG. 5, permits the two distal ends to lie inclose, touching proximity one to the other for insertion into soft tissue, muscle or in between bones which are to be spaced or separated. bringing the proximal ends of the arms 302 and 322 together spreads the distal ends and thus permits retraction of the soft tissue or the spreading apart of distinct bone structures.

An alignment assembly comprising an apertuerd bar 360, to which a plate 362 is secured by bolts 364 and 366, or some other suitable means. This keeps the arms in alignment but most importantly the aperture permits the bolt 112 or 132 as is desired to extend there through and to mount a retractor to the retractor support bar.

The procedure in which the present inventio nis used to very great advantage will now be described in order that the best mode of using the invention be fully described.

Anterior cervical fusion ahs been an accepted procedure for the treatment of cervical disc herniation as well as cervical spondylosis with associated cervical stenosis. Cervical spine fractures have also bee treated satisfactorily by the anterior approach. Although various types of grafts have been utilized, including kiel bone, cadaver bone and acrylic, it is generally accepted that atuogenous bone is superior in achieving a satisfactory fusion with less chance of resorption or infection.

The patient, under general anesthetic, is placed in the supine position with the head slightly turned to the left. The anterior cervical area is prepped and draped as a sterile field. Either the expanded field magnifying loupes or the operating microscope is utilizd throughout the procedure. Special instrumentation designed by the author is utilized at various stages or the procedure.

After prep and draping, a number 15 scalpel is used to make a 3 to 4 cm diagonal incision in the right anterior cervical area. The platysma muscle is identified and incised diagonally in the plane of its fibers and retracted laterally. A plane of dissection is then developed medial to the carotid sheath and lateral to the midline structures.

Utilizing a safety tipped 20 gauge spinal needle, x-ray identification of the exposed cervical disc space is carrier out. Manual soft tissue retractors are placed superior to the longus colli musculature bilaterally. The bipolar cautery is then used to cauterize the venous plexus usually present at the margins of the longus colli muscle bilaterally. With the undercutting curette or periosteal elevator, the longus colli muscle is elevated bilaterally and the Williams Self-Retaining Retractor then hooked under the muscle bilaterally. This specialized retractor can be dialed to the desired tension and the retractor blades articulated to achieve optimum exposure.

The involved disc space is then incised with a number 11 blade and the degenerated contents evacuated with the pituitary rongeur and small up biting curettes. Using a vertebral wedge, the vertebrae are distracted for placement of the vertebral spacer. The vertebral spacer is insertd into the disc space and turned 90° to open the space approximately 4–6 mm. The depth of the disc space is measured to determine the proper depth of incision. Safety-stop saw blades are chosen according to this measurement.

Figure 10A:
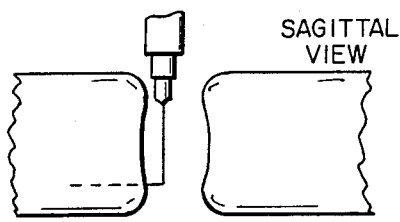
FIGS. 10a and 10b depict, respectively, the undercutting and vertical cuts for making the initial bone incision.
Figure 10B:
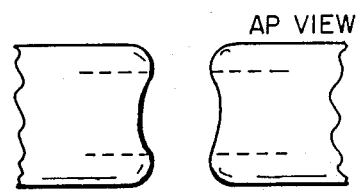
Figure 11A:
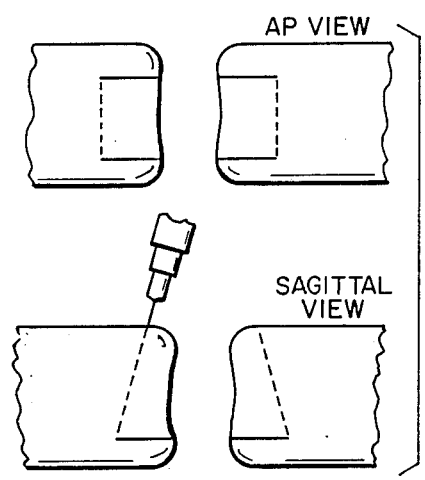
FIGS. 11a and 11b depict the completion of the bone incision and the removal of the bone graft components.

Utilizing the Williams Micro-Surgery Saw described in Ser. No. 26,038 U.S. Pat. No. 4,827,615 and undercutting right angle saw blade of the pre-measured depth, a horizontal cut (FIG. 10) is created approximately 2 mm to 3 mm from the posterior margin of the involved vertebral bodies. Following the horizontal under-cut, a safety-stop saw blade is used to create two bone incisions approximately 4 mm to 6 mm vertically on the superior vertebral body (FIG. 10a). Using a third selected safety stop saw blade for the transverse incision (FIG. 11a), the vertical incisions are then connected with a transverse incision. The blade is beveled at an angle from the cortex with the bevel being slightly wider at the base of the incision.

Figure 11B:
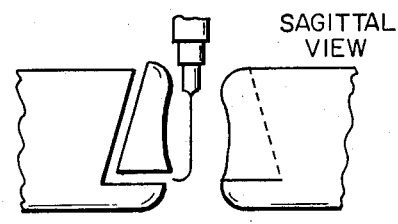

The rectangular graft is removed (FIG. 11b) and placed in a container with saline and blodd. Bleeding from the exposed bony surface is controlled with gelatin foam and tamponaded with cottoid sponges. The inferior vertebral body is prepared in the same manner.

Irrigation of the exposed wound is carried out and while awaiting hemostasis from the bone bleeding, attention is turned to fashioning a single bone graft.

Figure 12:
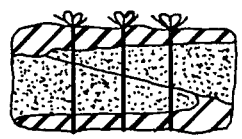

The two rectangular grafts are placed in opposition to each other with cancellous bone to cancellous bone. The wider cancellous end and narrow cortical end of each graft are opposed (FIG. 12). The single block graft is measured for length and width and then tied in the center with 2-0 Dexon interrupted suture. Three interrupted sutures are utilized with 2-0 Dexon interrupted suture. Three interrupted sutures are utilized in creating a solid block. The graft is then returned to the saline solution.

Returning to the exposed disc space, small curettes and a 2 mm ronguer are usd to remove remaining disc fragments and posterior ostcophytes. The posterior ostcophytes are removed in piecemeal fashion and the bone chips saved for later use. If possible, one third of the posterior longitudinal ligament is left intact.

After obtaining satisfactory decompression and upon passage of a regular blunthook into each foramen of the disc space, hemostatis is controlled with a layer of gelatin foam at the base of the boney opening. The rectangular opening in the vertebral bodies is measured with the Williams Gap Gauge.

Figure 13:
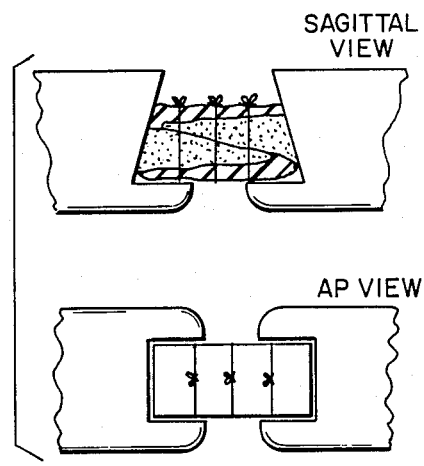

The single bone graft is trimmed accordingly and insertd into the interspace. Properly seated, the graft will be countersunk 2 mm to 3 mm below the anterior surface of the vertebral bodies (FIG. 13).

Upon satisfactory placement of the graft, the vertebral body spreader is slowly removed allowing compression and fixation of the bone graft. Gelatin foam is placed at the margins of the bony defect and the reserved bone chips layered over the graft site. A second gelatin foam square is placed over the bone chips.

The self-retaining retractor 300 is then relaxed and repositioned above the longus colli muscle exposing both muscles for reapproximation with two simple interrupted sutures. With satisfactory hemostasis accomplished, the self-retaining retractor 300 is removed and the platysma musculature reapproximatd with 3-0 Dexon simple interrupted sutures and the subcutaneous layer reapproximated with inverted 3-0 Dexon interrupted sutures. A 4-0 running subcuticular suture is carried out and betadine applied to the wound. Three small ¼ inch steri-strips are also used to reapproximate the skin edges and a dry, sterile dressing applied.

A rigid plastic cervical collar is placed on the patient before the patient is removed from the operating table and taken to the recovery room. The cervical collar is worn by the patient for approximately three to four months with gradual reduction of use as instructed. Interval AP and lateral x-rays are taken to monitor the progress of the fusion.

Anterior cervical fusion has long shown advantages for treating cervical disc herniation, cervical spondylosis and related stenosis. This procedure, utilizing autogenous bone from the cervical vertebrae, requires less anesthesia and operating time and greatly reduced the risk of cord trauma secondary to impaction. Regraft resorption and infection are also reduced and graft extrusion virtually eliminated.

Patients typically are ambulating the day of surgery, and are usually discharged within three to four hospital days instead of the standard eight to ten days. And the patient essentially obtains full post-operative range of motion of the cervical spine.

It is believed that with the foregoing explanation the operation of the retractors will be apparent. It will be apparent, for example, that the two mounting bars may be mounted in any angular relationship with one another. It will also be apparent that the retractors may be moved on the angular bar independently one of the other and that each of the retractors may be positioned along the length of the mounting bar at any desired location. It will also be apparent that the retractor assembly 300 can operate independently of as well as in conjunction with the mounting bars 302 and 322 in there articulated relationship.

Once the incision is made, and the muscular and other soft tissue has been retracted using,for example, retractor 200, then the fine soft structure may be retracted using the retractor 300. In addition, spacing of the discs of the spine may be accomplished, within a limited degree, by the retractor 300 which may be mounted to the same mounting bars as is the retractor 200. Alternatively, the retractor 300 may be used simply for spreading apart soft tissue.

It is believed apparent that there will be variations in the precise construction and details of this invention without departing from the spirit thereof.

Industrial Application

This invention find application is surgery generally including both human and animal surgery.

What is claimed is:

1. A tissue retractor for cervical fusion surgical procedures comprising, in combination:
   (a) a pair of elongat retractor mounting members each having a proximal and a distal end;
   (b) means connecting the proximal ends of the respective retractor mounting members pivotally together to permit relative articulation between such members and to clamp such members at any selected angle relative to each other;
   (c) retractor securing means; and
   (d) means mounting the retractor securing means on the respective retractor mounting members for movement reciprocally along the length of the retractor mounting members and positioning the rectractor securing means at a selected point thereupon; and
   (e) first and second retractors secured by the respective retractor securing means to the respective retractor mounting members, the first retractor comprising a blade and handle, the second retractor comprising a pair of elongate retractor arms pivotally connected together proximate the distal end and forming oppositely facing hooks on the distal end for engaging and retracting muscle during use.

2. A tissue retractor for cervical fusion surgery comprising, in combination:
   first and second elongate retractor mounting bars (102, 122) each having a proximal end and a distal end;
   first pivot means (140) mounting the proximal end of the mounting bars (102, 122) together for relative articulation;
   retractor holders (110, 130) for mounting tissue retractors to the respective retractor mounting bars (102, 122);
   adjustable securing members (104, 106 and 124, 126) mounting the retractor holders (110, 130) to the respective mounting bars (102, 122) and for moving the securing members (104, 106, 124, 126) to selected positions along the length of mounting members (102,122); and
   first and second retractors (200 or 300) secured to the retractor holders such that either of the retractors may be moved independently of the other along the length of the mounting members, at least one of the retractors comprising, in combination:
   a pair of elongate retractor arms (302, 322) each having a proximal end and a distal end;
   second pivot means (306, 308, 326, 328) securing adjacent sides of the retractor arms (302, 322) to each other between the ends of the retractor arms;
   meanss on the distal ends (304, 324) of the retractor arms for engaging and hooking the tissue of a patient, when the retractor is in use;
   means connecting the proximal ends (310, 330) of the retractor arms together and for moving the proximal ends (310, 330) toward and away from each other (312, 313, 340)
   such that movement of the proximal end of the retractor arms together moves the distal ends thereof apart and movement of the proximal ends apart moves the distal ends together.

3. The tissue retractor of claim 1 wherein at least one of the retractors comprises, in combination:
   a curved balde for engaging tissue and a handle mounted to the blade for moving the blade during use.

* * * * *